United States Patent [19]

Korshak et al.

[11] 4,167,546
[45] Sep. 11, 1979

[54] ADHESIVE COMPOSITION

[76] Inventors: Vasily V. Korshak, ulitsa Gubkina, 4, kv. 81; Antonina M. Polyakova, ulitsa Vavilova, 55/7, kv. 54; Maria D. Suchkova, ulitsa Obrucheva, 28, korpus 3, kv. 220; Kira A. Mager, Beskudnikovsky bulvar, 10, korpus 11, kv. 44, all of, Moscow, U.S.S.R.

[21] Appl. No.: 911,416

[22] Filed: May 30, 1978

[51] Int. Cl.² .................... C08F 214/18; C08L 35/04; C08L 35/08
[52] U.S. Cl. .................................. 525/275; 128/1 R; 204/159.16; 204/159.22; 428/304; 428/355; 526/247; 525/276; 525/266
[58] Field of Search ................ 526/247, 297; 260/881

[56] References Cited

U.S. PATENT DOCUMENTS

| | | | |
|---|---|---|---|
| 2,776,232 | 1/1957 | Shearer et al. | 526/297 |
| 3,004,960 | 10/1961 | Handy et al. | 526/247 |
| 3,465,045 | 9/1969 | Pittman et al. | 526/247 |
| 3,692,752 | 9/1972 | Setsuda et al. | 526/297 |
| 3,836,377 | 9/1974 | Delahunty | 526/297 |

*Primary Examiner*—Harry Wong, Jr.
*Attorney, Agent, or Firm*—Haseltine, Lake & Waters

[57] ABSTRACT

An adhesive composition based on a monomeric ester of α-cyanacrylic acid and a modifying agent, viz. a monomeric fluorinated ether of dimethylvinylethynylcarbinol of the formula:

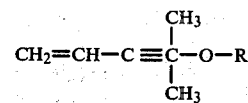

wherein R is $CH_2(CF_2)_nH$ or $CH_2(CF_2)_nCF_3$; n=2 to 10.

Owing to the addition of a monomeric fluorinated ether of dimethylvinylethynylcarbinol as a modifying agent into the adhesive composition, mechanical strength and water-resistant of the adhesive bond are improved. Thus, an ultimate shear strength of the adhesive bond produced from the adhesive composition according to the present invention after keeping in water for 10 days is equal to 119–185 kgf/cm².

4 Claims, No Drawings

4,167,546

ADHESIVE COMPOSITION

FIELD OF THE INVENTION

This invention relates to cold-curing adhesive compositions and, more specifically, to instant-effect adhesive compositions based on monomeric esters of α-cyanacrylic acid which have found an extensive use in various industries and in medicine.

BACKGROUND OF THE INVENTION

Known in the art is an adhesive composition containing at least 50% by weight of a monomeric ester of α-cyanacrylic acid, a modifying agent consisting of 1 to 49% by weight of a monomeric monofunctional (with one double bond) alkylacrylate and 1 to 15% by weight of a bifunctional (with two double bonds) monomer such as an alkylacrylate or divinylbenzene (cf. U.S. Pat. No. 2,816,093).

This prior art adhesive composition has a disadvantage residing in that an initiator should be added thereinto for curing which does not provide for a possibility of storing said composition, since it is unstable in the presence of an initiator. Furthermore, the use of said adhesive composition with the necessity of adding an initiator complicates the technology of bonding.

Also known in the art is an adhesive composition consisting of 20 to 95% by weight of a monomeric ester of α-cyanacrylic acid, 80 to 5% by weight of a modifying agent, viz, a monomeric methylenemalononitrile (cf. U.S. Pat. No. 2,763,585).

This prior art composition has a disadvantage residing in that it is readily hydrolyzable and, consequently, nonwater-resistant.

Another disadvantage of this prior art adhesive composition is that the second monomer, i.e., methylenemalononitrile, though enhancing adhesive properties of the monomeric ester of α-cyanacrylic acid (since it may be used per se as an adhesive), it forms, however, a rigid film and the ester of α-cyanacrylic acid should act as a plastifying agent therefor. Consequently, to obtain a flexible adhesive film, it is necessary to use a monomeric ester of α-cyanacrylic acid with a long-chain radical which is economically inefficient.

Still another disadvantage of this prior art adhesive composition resides in that the commercial-scale synthesis of methylenemalononitrile is very complicated.

Further known in the art is an adhesive composition consisting of 70 to 95% by weight of a monomeric ester of α-cyanacrylic acid and 30 to 5% by weight of a modifying agent, i.e., dimethylvinylethynylcarbinol or monomeric derivatives thereof of the formula:

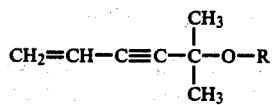

wherein R is H, CH₃, C₂H₅, C₄H₉, CH₂CH₂CN, COCH₃ and the like (cf. USSR Inventor's Certificate No. 280732).

Said adhesive composition has a high mechanical strength (150 kgf/cm²) and elasticity of the adhesive joint.

However, this adhesive composition also has an essential disadvantage which resides in its low water-resistance which restricts the field of its application.

SUMMARY OF THE INVENTION

It is an object of the present invention to provide such an adhesive composition which forms an adhesive bond possessing, in addition to a high mechanical stength, an adequate water-resistance.

This object is accomplished by an adhesive composition based on a monomeric ester of α-cyanacrylic acid and a modifying agent, viz, a monomeric fluorinated ether of dimethylvinylethynylcarbinol of the formula:

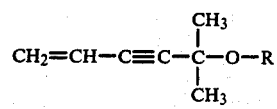

wherein R is $CH_2(CF_2)_nH$ or $CH_2(CF_2)_nCF_3$; n=2 to 10.

It is preferable that the adhesive composition according to the present invention would incorporate the following proportions of the components, percent by weight: monomeric ester of α-cyanacrylic acid—70 to 95 monomeric fluorinated ether of dimethylvinylethynylcarbinol—30 to 5.

Kinematic viscosity of the adhesive composition containing its ingredients in the above-specified proportions is equal to 2–5 cStokes.

In some cases, e.g., in bonding of porous surfaces, it is advisable to employ a more viscous adhesive composition which contains, in addition to the above-mentioned monomeric esters, also polymers of said esters (homopolymers, copolymers or mixtures thereof); kinematic viscosity of the composition in this case should be varied within the range of from 15 to 100 cStokes.

Presence of said polymers in the adhesive composition is achieved by a partial polymerization thereof, e.g., by means of UV-irradiation.

To prevent the monomers from a further polymerization, the resulting adhesive composition according to the present invention is added with an inhibitor of the radical polymerization in an amount ranging from 0.04 to 0.06% by weight of to adhesive composition. As the inhibitor use can be made of hydroquinone or methyl ether of hydroquinone.

DETAILED DESCRIPTION OF THE INVENTION

The present invention is embodied in the following manner.

A monomeric ester of α-cyanacrylic acid containing a stabilizing agent, usually sulphur dioxide, is mixed, in a polyethylene flask, in an atmosphere of a dry inert gas such as nitrogen, helium, argon with a modifying agent, i.e., monomeric fluorinated ether of dimethylvinylethynylcarbinol. The polyethylene flask with the mixture is sealed and stored in a cooler at a temperature of at most 7° C. As the monomeric esters of α-cyanacrylic acid use may be made, for example, of ethyl ester of α-cyanacrylic acid, butyl ester of α-cyanacrylic acid, n-hexyl ester of α-cyanacrylic acid, benzyl ester of α-cyanacrylic acid.

To improve water-resistance of the adhesive composition according to the present invention, it is advisable to take the components in the following proportions, percent by weight: monomeric ester of α-cyanacrylic acid—70 to 95, monomeric fluorinated ether of dimethylvinylethynylcarbinol—30 to 5. Kinematic viscosity of the composition is equal to 2-5 cStokes.

As the modifying agent, i.e., a monomeric fluorinated ether of dimethylvinylethynylcarbinol of the above-given generic formula use can be made of, for example, 1,1,3-trihydroperfluoropropyl ether of dimethylvinylethynylcarbinol, 1,1,7-trihydroperfluoroheptyl ether of dimethylvinylethylnylcarbinol, 1,1,11-trihydroperfluoroundecyl ether of dimethylvinylethynylcarbinol, 1,1-dihydroperfluorobutyl ester of dimethylvinylethynylcarbinol. The above-specified modifying agent is prepared by reacting corresponding fluorinated alcohols with dimethylvinylethynylcarbinol in the presence of a catalyst, i.e., sulphuric acid and a radical-polymerization inhibitor, i.e., hydroquinone.

In certain cases, for example, in bonding of porous surfaces, it is suitable to use a more viscous adhesive composition. To this end, the starting components are mixed in a quartz vessel in a current of an inert gas such as argon. After mixing, the resulting adhesive composition is subjected to a partial polymerization which is effected, e.g. by means of UV-irradiation. The irradiation can be performed, e.g., by means of a 300–1,000 W mercury-quartz lamp at the distance of 30 mm from the irradiation source with cooling of the vessel by means of tap water. As a result of the irradiation, the adhesive composition contains, in addition to the above-mentioned esters, also homopolymers or copolymers of said monomers or a mixture thereof formed during the partial polymerization. Kinematic viscosity of the composition in this case is varied within the range of from 15 to 100 cStokes. Then, to prevent a further polymerization of the monomers, an inhibitor of the radical polymerization is added into the thus-prepared adhesive composition in an amount of from 0.04 to 0.06% by weight of the adhesive composition. As the radical-polymerization inhibitor use can be made of hydroquinone or methyl ether or hydroquinone.

Owing to the addition of a monomeric fluorinated ether of dimethylvinylethynylcarbinol into the adhesive composition as a modifying agent, the ultimate mechanical strength of the adhesive bond is increased. Upon testing of samples made of duralumine bonded by means of an adhesive composition containing non-fluorinated modifying agent such as propyl ether of dimethylvinynylethynylcarbinol, the ultimate shear strength of the adhesive bond after keeping in water for 10 days is 20 to 25 kgf/cm$^2$, whereas the ultimate shear strength of an adhesive bond produced by means of a composition containing a fluorinated modifying agent of the above-mentioned generic formula after keeping in water for 10 days is within the range of from 119 to 185 kgf/cm$^2$.

The adhesive composition according to the present invention finds an extensive use in various branches of industry. Thus, this adhesive composition is used in radio engineering for fixation of radio components, in electronics for assembling parts and components of electronic instruments, in ore-extraction industry for securing sensors for measurements of tensions of various rocks. Besides, the adhesive composition according to the present invention may find its application in medicine for a sutureless bonding of tissues of a living organism upon surgical operations.

For a better understanding of the present invention the following specific Examples are given hereinbelow by way of illustration.

EXAMPLE 1

Preliminary prepared is 1,1,3-trihydroperfluoropropyl ester of dimethylvinylethynylcarbinol. To a mixture consisting of 100 g (0.75 mole) of 1,1,3-trihydroperfluoropropanol, 2.5 ml of a concentrated sulphuric acid used as a catalyst and 0.5 g of hydroquinone as a polymerization inhibitor, there are gradually poured 5.5 g (0.5 mole) of dimethylvinylethynylcarbinol upon a vigorous stirring and cooling of the resulting mixture with ice-cold water. Then the mixture is heated to the temperature of 50° C. and maintained at this temperature for 3 hours. Thereafter, the reaction mixture is cooled, separated from water evolved during the reaction, neutralized with a saturated solution of sodium bicarbonate, washed with water to a netural reaction, and dried over anhydrous sodium sulphate. Afterwards, a fraction with the boiling point of 75°–80° C. (30 mm Hg) and refraction index of $n_D^{20} = 1.4067$ is isolated by way of fractionation in vacuum in the amount of 88.3 g (70% of the theoretical value as calculated for the reacted carbinol). After a repeated distillation the product has its boiling point of 38°–40° C. (1 mm Hg), refraction index $n_D^{20} = 1.4068$–1.4070; specific gravity $d_4^{20} = 1.104$.

The resulting 1,1,3-trihydroperfluoropropyl ether of dimethylvinylethynylcarbinol comprises a colourless liquid with the elemental structure corresponding to the formula:

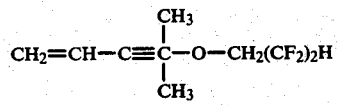

Found, % by weight: C 53.68 H 5.47 F 33.8. $C_{10}H_{12}F_4O$. Calculated, wt.%: C 53.60 H 5.40 F 33.90.

IR-spectrum of this compound has absorption bands in the region of 2,220 cm$^{-1}$ corresponding to valency oscillations of the —C≡C— bond, in the region of 1,600 cm$^{-1}$ corresponding to the —C═CH bond; it also has intensive bands in the region of 1,345; 1,200 and 1,100 cm$^{-1}$ characteristic of CF— groups. The absorption band in the region of 3,400 cm$^{-1}$ characteristic of OH groups is not present at all.

80 g of monomeric ethyl ester of α-cyanacrylic acid are mixed in the atmosphere of dry argon in a polyethylene flask with 20 g of 1,1,3-trihydroperfluoropropyl ether of dimethylvinylethynylcarbinol. Then the flask with the mixture is sealed and kept in a cooler at a temperature of at most 5° C.

The resulting adhesive composition has the following properties:
  ultimate shear strength of the adhesive bond as tested on duralumin samples at the temperature of 20° C., kgf/cm$^2$—170
  ultimate shear strength of the adhesive bond at the temperature of 20° C. on duralumin samples after keeping them in water for 10 days, kgf/cm$^2$—130
  kinematic viscosity, cStokes—3.

The adhesive composition of this Example can be used, for example, in tensometry.

EXAMPLE 2

1,1,7-Trihydroperfluoroheptyl ether of dimethylvinylethynylcarbinol is preliminary prepared. The synthesis of this ester is performed following the procedure described in the foregoing Example 1, except that as the starting fluorinated alcohol use is made of 1,1,7-trihydroperfluoroheptyl alcohol.

The resulting compound comprises a colourless liquid with the structural composition corresponding to the formula:

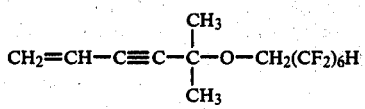

Boiling temperature of said compound is 93°–95° C. (7 mm Hg); refraction index is $n_D^{20} = 1.3780$; density $d_4^{20} = 1.3892$.

90 g of butyl ester of α-cyanacrylic acid are mixed with 10 g of 1,1,7-trihydroperfluoroheptyl ether of dimethylvinylethynylcarbinol in the atmosphere of dry nitrogen in a quartz vessel. The resulting adhesive composition is exposed to UV-irradiation from a 300 W quartz-mercury lamp at the distance of 30 cm for the period of 4 hours upon cooling of the vessel with running water. Then the thus-prepared composition is added with 0.05 g of hydroquinone. The adhesive composition is poured into a polyethylene flask and stored in a cooler at the temperature of 5° C.

The resulting adhesive composition has the following properties:
Ultimate shear strength of the adhesive bond on samples of duralumin at the temperature of 20° C., kgf/cm²—150
Ultimate shear strength of the adhesive bond on samples of duralumin at the temperature of 20° C. after keeping in water for 10 days, kgf/cm²—130.
kinematic viscosity, cStokes—30.

The adhesive composition prepared according to this Example is useful for bonding porous surfaces such as upon renovation of pictures, sculptures and the like.

EXAMPLE 3

1,1,11-Trihydroperfluoroundecyl ether of dimethylvinylethynylcarbinol is preliminary prepared. The synthesis of this ester is performed following the procedure described in the foregoing Example 1, except that as the starting fluorinated alcohol use is made of 1,1,11-trihydroperfluoroundecyl alcohol. The resulting product comprises a compound corresponding to the formula:

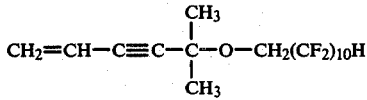

95 g of n-hexyl ester of α-cyanacrylic acid are mixed with 5 g of 1,1,11-trihydroperfluoroundecyl ether of dimethylvinylethynylcarbinol in the atmosphere of dry helium in a quartz vessel. The thus-prepared adhesive composition is exposed to UV-irradiation by means of a 1,000 W mercury-quartz lamp at the distance of 30 cm for the period of 2 hours upon cooling of the vessel with running water.

Then, the resulting composition is added with 0.05 g of methyl ether of hydroquinone. The adhesive composition is poured into a polyethylene flask and kept in a cooler at the temperature of 5° C.

The thus-prepared adhesive composition has the following properties:
Ultimate shear strength of the adhesive bond on samples of duralumin at the temperature of 20° C., kgf/cm²—120
Ultimate shear strength of the adhesive bond on samples of duralumin at the temperature of 20° C. after keeping in water for 10 days, kgf/cm²—110
kinematic viscosity, cStokes—15.

EXAMPLE 4

1,1-Dihydroperfluorobutyl ester of dimethylvinylethynylcarbinol is preliminary prepared. The synthesis of this ester is conducted following the procedure described in the foregoing Example 1, except that as the starting fluorinated alcohol use is made of 1,1-dihydroperfluorobutyl alcohol.

The resulting compound comprises a colourless liquid with the elemental structure of the formula:

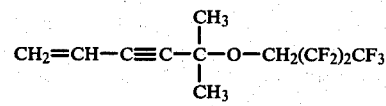

95 g of ethyl ester of α-cyanacrylic acid and 5 g of 1,1-dihydroperfluorobutyl ester of dimethylvinylethynylcarbinol are mixed in the atmosphere of nitrogen in a quartz vessel.

The resulting adhesive composition is exposed to UV-irradiation from a 1,000 W mercury-quartz lamp at the distance of 30 cm for the period of 2 hours upon cooling of the vessel with water. After the irradiation hydroquinone is added in the amount of 0.05 g.

The adhesive composition is poured into a polyethylene flask and kept in a cooler at the temperature of 5° C.

The resulting adhesive composition has the following properties:
Ultimate shear strength of the adhesive bond on samples of duralumin at the temperature of 20° C., kgf/cm²—190
Ultimate shear strength of the adhesive bond on samples of duralumin at the temperature of 20° C. after keeping in water for 10 days, kgf/cm²—185
kinematic viscosity, cStokes—100.

The adhesive composition of this Example is useful in bonding of jewelry.

EXAMPLE 5

1,1-Dihydroperfluorododecyl ether of dimethylvinylethynylcarbinol is preliminary prepared. The synthesis of this ester is carried out following the procedure described in the foregoing Example 1, except that as the starting fluorinated alcohol use is made of 1,1-dihydroperfluorododecyl alcohol.

The resulting compound corresponds to the formula:

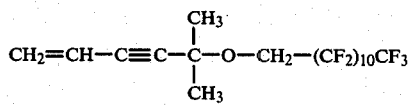

70 g of butyl ester of α-cyanacrylic acid and 30 g of 1,1-dihydroperfluorododocyl ether of dimethylvinylethynylcarbinol are mixed in the atmosphere of dry helium in a quartz vessel. The resulting adhesive composition is exposed to UV-irradiation from a 1,000 W mercury-quartz lamp at the distance of 30 cm for the period of 2 hours upon cooling of the vessel with running water. After the irradiation there is added 0.04 g of methyl ether of hydroquinone. The adhesive composition is poured into a polyethylene flask and kept in a cooler at the temperature of 5° C.

The resulting adhesive composition has the following properties:

Ultimate shear strength of the adhesive bond on samples of duralumin at the temperature of 20° C., kgf/cm$^2$—160

Ultimate shear strength of the adhesive bond on samples of duralumin at the temperature of 20° C. after keeping in water for 10 days, kgf/cm$^2$—140 kinematic viscosity, cStokes—50.

The adhesive composition prepared according to this Example may be useful for bonding jewelry as well as for sutureless bonding of tissues of a living organism upon surgical operations.

What is claimed is:

1. An adhesive composition based on a monomeric ester of α-cyanacrylic acid selected from the group consisting of ethyl ester, butyl ester, n-hexyl ester and benzyl ester and a modifying agent, which is a monomeric fluorinated ether of dimethylvinylethylnylcarbinol of the formula:

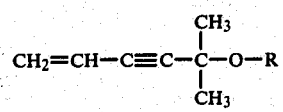

wherein R is $CH_2(CF_2)_nH$ or $CH_2(CF_2)_nCF_3$; n=2 to 10, wherein said composition consists of 70 to 95% by weight of said monomeric ester of α-cyanacrylic acid and 30 to 5% by weight of said monomeric fluorinated ether of dimethylvinylethynylcarbinol with the kinematic viscosity of the composition variable within the range of from 2 to 5 centi Stokes.

2. An adhesive composition as in claim 1, further comprising in addition to said monomeric esters, polymers of said esters; with kinematic viscosity of the composition variable within the range of from 15 to 100 centi Stokes.

3. An adhesive composition as in claim 2, further comprising a radical-polymerization inhibitor in an amount of 0.04–0.06% by weight of the adhesive composition.

4. An adhesive composition as in claim 3, containing, as the radical-polymerization inhibitor, a compound selected from the group consisting of hydroquinone and methyl ester of hydroquinone.

* * * * *